United States Patent [19]

Ansmann et al.

[11] Patent Number: 5,676,955
[45] Date of Patent: Oct. 14, 1997

[54] LOCAL ANESTHETIC

[75] Inventors: Achim Ansmann, Erkrath; Ansgar Behler, Bottrop; Rolf Franke, Reinbeck b. Hamburg; Peter Schmersahl, Barsbuettel/Hamburg, all of Germany

[73] Assignee: Henkel Kommanditgesellschaft auf Aktien, Duesseldorf, Germany

[21] Appl. No.: 469,038

[22] Filed: Jun. 6, 1995

Related U.S. Application Data

[62] Division of Ser. No. 50,323, May 10, 1993.

[30] Foreign Application Priority Data

Nov. 9, 1990 [DE] Germany .................... 40 35 682.5

[51] Int. Cl.$^6$ ........................................ A61K 7/48
[52] U.S. Cl. ..................... 424/401; 424/59; 424/65; 424/701; 514/817; 514/818
[58] Field of Search ................. 424/401, 59, 65, 424/701; 514/817, 818

[56] References Cited

U.S. PATENT DOCUMENTS 4,912,874  4/1990  Franke et al. .................... 514/552

Primary Examiner—Jyothsan Venkat
Attorney, Agent, or Firm—Wayne C. Jaeschke; John E. Drach; Henry E. Millson, Jr.

[57] ABSTRACT

This invention relates to a mixture of homologous narrow range lauryl polyglycol ethers, to its use as a local anaesthetic agent.

2 Claims, No Drawings

LOCAL ANESTHETIC

This application is a division of Ser. No. 08/050,323 filed May 10, 1993, which is a 371 of PCT/EP91/02075 Nov. 4, 1991.

BACKGROUND OF THE INVENTION

1. Field of the Invention

This invention relates to a mixture of homologous narrow-range lauryl polyglycol ethers, to its use as a local anaesthetic agent in therapeutic preparations for treatment of the human body and as an irritation-reducing component in hair and skin care and cleaning preparations.

2. Statement of Related Art

The local anaesthetic effect of homologous alkyl polyglycol ethers has been known for some time (cf. for example, K. Soehring, M. Frahm and K. Mletzko: Arch. int. pharmacodyn. 91 112 (1952) or H. F. Zipf, E. Ch. Dittmann: Naunyn Schmiedebergs Arch. exp. Path. u. Pharmak. 247, 544 to 557 (1964). The adducts of approx. 9 mol ethylene oxide with n-lauryl alcohol are recognized as the most effective compounds. These adducts are mixtures of homologous polyglycol ethers which have an average degree of ethoxylation of 9, but a broad homolog distribution, the homologs containing 8, 9 and 10 glycol ether groups making up no more than, in all, 30 to 40% by weight of the mixture. At the same time, more than 30% by weight lower and higher homologous polyglycol ethers and free lauryl alcohol are present in the mixture. One product of this type is commercially available as a local anaesthetic under the name of "polydocanol" or "Thesit®".

Known local anaesthetics of the polydocanol type are limited in their effect. They also have certain side effects. In particular, contact allergies have occurred in individual cases, having been assumed to be caused inter alia by secondary products of technical polydocanol. Accordingly, there was a need for a product of chemically uniform composition.

Numerous processes for the production of narrow-range alkyl polyglycol ethers have become known in the meantime. The ethylene oxide adducts produced by these processes consist very largely of homologs containing x−1, x and x+1 glycol ether groups where x is the number of mols ethylene oxide added on per mol alkanol. Most of these processes comprise adding the ethylene oxide in the presence of a catalyst which is an oxide, hydroxide or salt of an alkaline earth metal.

DESCRIPTION OF THE INVENTION

It has now been found that mixtures of homologous lauryl polyglycol ethers corresponding to formula I

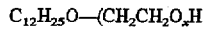

$$C_{12}H_{25}O-(CH_2CH_2O)_xH$$

in which $C_{12}H_{25}$ is a linear primary alkyl group and x has an average value of 5 to 7, at least 75% by weight of the homolog mixture consisting of homologs with x=4 to 8 glycol ether groups, have an unexpectedly high local anaesthetic effect compared with the known local anaesthetic polydocanol.

A particularly effective local anaesthetic is a lauryl polyglycol ether of formula I which has an average degree of ethoxylation x of 6.5 and which contains less than 15% by weight homologs having a degree of ethoxylation of 0 to 4 and less than 10% by weight homologs having a degree of ethoxylation of 9 and more.

The mixture of homologous lauryl polyglycol ethers of formula I according to the invention may be produced by any of the known ethoxylation processes which give narrow-range ethoxylates. Such processes are described, for example, in EP-A-6 105, EP-A-18 463, EP-A-20 867, EP-A-33 359, EP-A-46 582, EP-A-46 947, EP-A-82 554, EP-A-95 562 or EP-A-321 053 and in German patent application P 40 03 658.8.

A particularly preferred process for the production of such ethoxylates is described in EP-A-339 426. In this preferred production process, the mixture of homologous lauryl polyglycol ethers according to the invention is prepared by addition of 5 to 7 mol and preferably 6.5 mol ethylene oxide onto 1 mol n-dodecan-1-ol in the presence of calcined hydrotalcites as catalysts. Small quantities of polyethylene glycol and high molecular weight ethoxylates can be removed from the liquid ethoxylate by filtration.

The mixture of homologous lauryl polyglycol ethers of formula I according to the invention has a very good local anaesthetic effect. The limiting concentration in water to achieve the local anaesthetic threshold value is only half as high as that of the known local anaesthetic polydocanol (n-dodecan-1-ol/poly(9EO)glycol ether mixture). The action spectrum encompasses both external and endogenous local anaesthesia. Accordingly, the main fields of application are antipruritic, anti-eczema and haemorrhoidal preparations.

By virtue of the minimal side effects, topical cosmetic application above all is of significance in addition to purely therapeutic application. Accordingly, the present invention also relates to the use of the mixture of homologous lauryl polyglycol ethers according to the invention as an irritation-reducing component in cosmetic hair and skin care and cleaning preparations.

Cosmetic preprarations of the type in question are, for example, sunscreen preparations, skin creams, shower preparations, bath additives, liquid soaps, shampoos, deodorants and antiperspirant preparations and also oral hygiene and dental care preparations.

In addition, the mixture of homologous lauryl polyglycol ethers of formula I according to the invention has very good emulsifier properties. Accordingly, it is particularly suitable for the production of cosmetic preparations of the type mentioned above which contain skin-compatible, refatting oil components in emulsifiable, emulsified or solubilized form. In cases such as these, the lauryl polyglycol ether mixtures simultaneously develop an emulsifying effect and an irritation-reducing effect.

In one particularly preferred embodiment, therefore, the invention relates to medicinal bath preparations and personal hygiene preparations which contain physiologically compatible oil components and, as emulsifiers, at least one mixture of homologous lauryl polyglycol ethers corresponding to formula I. The mixture of homologous lauryl polyglycol ethers according to the invention may be present in a quantity of 0.05 to 1 part by weight per part by weight of the oil or fatty component.

Preferred physiologically safe oils are oil components and mixtures of oils with fats and waxes which are still liquid at +20° C. Examples of such oil components are oleyl alcohol, 2-octyl dodecanol, 2-hexyl decanol, paraffin oils, isopropyl myristate, isopropyl palmitate, decyl oleate, isooctyl stearate, oleyl oleate, decyl erucate, natural liquid wax esters, such as sperm oil and jojoba oil, and synthetic analogs, but above all fatty acid triglycerides based on $C_{8-22}$ fatty acids, for example caprylic and/or capric acid triglyceride, oleic acid triglyceride, liquid natural triglyceride oils such as, for example, olive oil, soybean oil, sunflower oil, peanut oil, almond oil, avocado oil, hazelnut oil and wheat germ oil. Finally, dicarboxylic acid esters such as, for example, dibutyl sebacate, dioctyl adipate, the full esters of diols or polyols, for example the fatty acid $C_{8-18}$ esters of ethylene glycol, 1,2-propylene glycol, butanediol, hexanediol, neopentyl glycol, trimethylol propane and pentaerythritol and the complex esters of dicarboxylic acids, diols (or polyols) and fatty acids.

The medicinal bath preparations and personal hygiene preparations may be present, for example, as emulsion concentrates which contain very little, if any, water and which emulsify spontaneously on addition to bath water. However, they may also be present as emulsions or solubilizates already containing water as outer phase.

To prepare the spontaneously emulsifiable emulsion concentrates, it may be necessary to use other emulsifiers and, optionally, co-emulsifiers to achieve good dispersibility of the bath preparations in water and the formation of a stable emulsion. In addition, other pharmaceutical dermatological or cosmetic agents, fragrances, antioxidants, thickeners, solubilizers, complexing agents and buffer salts for pH adjustment may also be present.

The invention is illustrated by the following Examples.

EXAMPLES

1a) Preparation of dodecanol poly-(6,5)-glycol ether (NRE) in accordance with EP 339 426 A2, Example 1

A commercially available synthetic hydrotalcite was calcined for 8 h at 500° C. To react a commercially available lauryl alcohol with 6.5 mol ethylene oxide, 1.860 kg lauryl alcohol were introduced into a pressure reactor and 24 g of the calcined hydrotalcite obtained beforehand were added. The reactor was purged with nitrogen and evacuated for 30 minutes at a temperature of 100° C. The temperature was then increased to 180° C. and 2.860 kg ethylene oxide were introduced under a pressure of 4 to 5 bar. After termination of the reaction, the mixture was left to react for 30 minutes. Removal of suspended catalyst by filtration left the required mixture of homologous alkyl polyglycol ethers. The product had the following characteristic data:

Hydroxyl value: 122

$n_D^{50}$: 1.4449

$D_{70}$ : 0.950

Cloud point 56°C. (1% by weight in water)

pH value: 6.8 (1% by weight in water)

1 b) Preparation of dodecanol poly-(6,5)-glycol ether in accordance with German patent application P 40 03 658.8

6 g strontium phosphate calcined at 260° C. were dissolved in 235.7 g dodecanol (1.25 mol). The solution was transferred to an autoclave which was purged with nitrogen and then evacuated for 30 minutes at 100° C. Ethylene was then introduced under a pressure of 5 bar while heating to at most 180° C. 364.3 g (8.2 mol) ethylene oxide were taken up in portions over a period of 4 hours. After the ethylene oxide had been added, the temperature was kept at 170°C. for 30 minutes (after-reaction time). The catalyst was then removed through a pressure filter (max. 3 bar) while cooling to room temperature. The yield was 557 g. The hydroxyl value was 120.2.

The products had the following homolog distribution:

| | 1a | 1b |
|---|---|---|
| Dodecanol | 0.2% by weight | 1.5% by weight |
| Dodecanal monoglycol ether | 0.2% by weight | 1.9% by weight |
| Dodecanol diglycol ether | 1.0% by weight | 2.9% by weight |
| Dodecanol tetraglycol ether | 8.0% by weight | 8.9% by weight |
| Dodecanol pentaglycol ether | 18.0% by weight | 14.8% by weight |
| Dodecanol hexaglycol ether | 25.0% by weight | 19.0% by weight |
| Dodecanol heptaglycol ether | 22.0% by weight | 19.2% by weight |
| Dodecanol octaglycol ether | 13.0% by weight | 15.7% by weight |
| Dodecanol nonaglycol ether | 6.0% by weight | 9.8% by weight |
| Dodecanol decaglycol ether | 3.0% by weight | 3.5% by weight |
| higher polyglycol ethers | 3.7% by weight | 2.8% by weight |

2. Local anaesthetic effect

The local anaesthetic effect was determined by the cornea reflex test on rabbits' eyes. This method was first published by M. J. Regnier (C.R. Acad. Sci. Paris 177, 558 to 560, 1923) (cf. also Th. Eckert, E. Wachtel, Arzneimittelforschung / Drug Res. 33, 98 to 100, 1983). The basis of this test is that the number of irritations carried out with a brush up to the first complete blink is proportional to the degree of anaesthesia reached. If there is no lid closure after 100 irritations (at intervals of 4 seconds), anaesthesia is complete.

The limiting concentration in water at which a local anaesthetic theshold value (50 irritations without blinking) is reached was determined. This limiting concentration was at 1:145,000 (approx. $6.9 \cdot 10^{-6}$) for the product of Example 1. For polydocanol (Thesit®, n-dodecan-1-ol +9 EO, normal range), the limiting concentration is at 1:70,000 ($1.4 \cdot 10^{-5}$).

3. Application Example

A spontaneously emulsifiable bath oil according to the invention having the following composition was prepared:

soybean oil: 85% by weight product of Example 1: 15% by weight

For comparison, a bath oil was prepared from 85% by weight soybean oil and 15% by weight polydocanol (normal range). Both products were dispersed in water and the local anaesthetic effect of a dilution series was determined as described in 2. until the limiting concentration was reached.

Bath oil according to the invention: limiting concentration 1:22,000

Comparison product containing polydecanol: limiting concentration 1:8,000

What is claimed is:

1. A composition consisting essentially of from about 0.05 to about 1 part by weight based on the oil, of a mixture of homologs of lauryl polyglycol ether corresponding to the formula I $$C_{12}H_{25}O\text{—}(CH_2CH_2O)_x\text{—}H \qquad I$$

wherein $C_{12}H_{25}$ is a linear primary alkyl group and x is a number having an average value of from about 5 to about 7, wherein at least 75% by weight of said mixture consists of compounds of formula I wherein x has a value of from 4 to about 8, and a physiologically safe oil which is in the liquid state at 20° C.

2. A process for anesthtizing an exterior surface the body of a mammal which comprises applying to said surface an effective amount of a composition consisting essentially of a physiologically safe oil and a mixture of homologs of lauryl polyglycol ether corresponding to the formula I $$C_{12}H_{25}O-(CH_2CH_2O)_x-H \qquad (I)$$

wherein $C_{12}H_{25}$ is a linear alkyl group and x is a number having an average value of from about 5 to about 7, wherein at least 75% by weight of said mixture consists of compounds of formula I wherein x has a value of from about 4 to about 8, and wherein the concentration of the mixture of homologs of lauryl polyglycol ether of formula I in the composition is from about 0:05 parts to about 1.0 parts by weight, based on the weight of the oil.

* * * * *